United States Patent [19]

Buehler et al.

[11] 4,117,116

[45] Sep. 26, 1978

[54] METHOD FOR LOWERING THE VISCOSITY OF CERTAIN AGENTS

[75] Inventors: John D. Buehler, Fort Washington; Pravinchandra B. Shah, Willow Grove, both of Pa.; Robert S. Joslin, Northbrook, Ill.

[73] Assignee: William H. Rorer, Inc., Fort Washington, Pa.

[21] Appl. No.: 561,766

[22] Filed: Mar. 31, 1975

Related U.S. Application Data

[63] Continuation of Ser. No. 395,472, Sep. 10, 1973, abandoned.

[51] Int. Cl.$^2$ .................................................. A61K 33/08
[52] U.S. Cl. ........................................ 424/157; 424/158
[58] Field of Search .................................. 424/157, 158

[56] References Cited

U.S. PATENT DOCUMENTS

| 1,936,364 | 3/1933 | Pasternack et al. | 424/157 |
| 2,843,521 | 7/1958 | Entrekin | 424/157 |
| 3,155,577 | 11/1964 | Mercer et al. | 424/158 |
| 3,347,744 | 10/1967 | Latshaw et al. | 424/157 |
| 3,579,634 | 5/1971 | Brown | 424/158 |
| 3,591,680 | 7/1971 | Greene et al. | 424/158 |
| 3,735,007 | 7/1973 | Lapidus et al. | 424/158 |

FOREIGN PATENT DOCUMENTS 1,031,149  5/1966  United Kingdom ........................ 424/157

*Primary Examiner*—Frederick E. Waddell
*Attorney, Agent, or Firm*—James A. Nicholson; Raymond Underwood

[57] ABSTRACT

This invention describes a method of lowering the viscosity of aqueous gels of agents used in pharmaceutical preparations and of aqueous suspensions used as pharmaceutical preparations. Particular gels and suspensions and the viscosity lowering ingredients which are most useful are also described.

6 Claims, No Drawings

METHOD FOR LOWERING THE VISCOSITY OF CERTAIN AGENTS

This application is a continuation of Ser. No. 395,472, now abandoned, filed by us on Sept. 10, 1973 having this same title.

This invention relates to methods of reducing the viscosity of gels and more particularly it is concerned with increasing the flowability of aqueous suspensions of pharmaceutical agents used as gastric antacids.

The agents are the ones commonly administered to persons suffering from gastric hyperacidity, dyspepsia, peptic ulcers, constipation and the like. The agents usually used for these purposes are magnesium hydroxide, aluminum hydroxide and their mixtures.

The invention is concerned with the commercially available aqueous concentrations of these agents rather than with their dry powders. In the form generally supplied by manufacturers these preparations are 25 to 40% W/W aqueous concentrations and they are such stiff gels or pastes that they will not flow. In fact, if a shovel is used to remove a segment of it from a bulk mass, the remaining portion will not flow into the void. This bulk material cannot be forced to flow through a pipe or conduit unless an extremely high pressure is applied.

The present invention resides in the discovery that certain ingredients may be added to this concentrated mass of magnesium hydroxide and/or aluminum hydroxide to bring about a marked reduction in its viscosity. The remarkable feature is that a concentration of only about a few percent W/W of one of the ingredients achieves an unexpected lowering of the slurry's viscosity. An essential requirement of these ingredients is that they must be physiologically acceptable to humans. As these ingredients must remain in the final preparations to be swallowed by the patient it is essential that they be non-toxic.

The lowering of the viscosity which is obtained by practicing the invention is of considerable value in commercial operations. Concentrations containing magnesium hyroxide and/or aluminum hydroxide, which would require bulk handling as with a shovel, can be made flowable by the addition of one of the ingredients listed below, so that it can be pumped through conduits. It can be delivered, for instance, to drying apparatus such as a spray dryer, or it can be supplied to bottle filling machines for direct filling in consumer bottles.

The present invention may be practiced with ease using commercially available gelis having a putty-like consistency. They would have to be diluted considerably by the addition of water to make them sufficiently flowable for pumping through pipes. If this means that there is too much water present for the diluted preparation to be usable as a final consumer product, the excess water would have to be removed. The present invention eliminates the need to add diluting water which may have to be subsequently removed.

Another important aspect of this invention is that the increased flowability of the suspensions thereby allows for more concentrated suspensions. The result of the viscosity lowered suspensions is that the relatively reduced amount of water present means that there is less water to be removed if further concentration is to be carried out, such as by a drying operation. An ordinary slurry containing magnesium hydroxide and/or aluminum hydroxide is difficult to spray dry and the same can be converted to a suspension which then can be easily spray dried by the method of this invention.

The viscosity lowering feature of this invention, from another viewpoint, is its concentration increasing effect as mentioned above and this has the advantage of producing, for example, a concentrated milk of magnesia. The ordinary preparation which is taken as a laxative is diluted and several tablespoons of it may be called for. The reduced viscosity, or the increased concentration of the suspensions of this invention allows a smaller volume to be taken. This is also true of any concentrated form of the above suspensions.

The viscosity lowering ingredients, also called fluidizing agents, which are encompassed by this invention include acacia or gum arabic, citric acid, sodium citrate, sodium lauryl sulphate and dioctyl sodium sulfosuccinate. They may be present in the ratio of 0.05 to 5.0% in a weight to weight basis of the fluidizing agent to total weight of the suspension or gell. A preferred ratio is 0.10 to 4.0% on a W/W basis in the composition.

The following representative examples describe how the viscosity reducing methods of the invvention may be practiced. In these Examples, the reported viscosity was measured with a Brookfield Viscometer using spindle No. 3 at 12 r.p.m.

EXAMPLE 1

Viscosity Reduction of Magnesium Hydroxide Gel Cake

The following materials are combined and thoroughly blended in a suitable mixer:

Magnesium hydroxide wet gel cake (30%) — 980 g.
Acacia — 20 g.
Resultant viscosity: (under stress) 3000 cps.

The viscosity of the initial commercial wet gel with no acacia added cannot be measured with the Brookfield Viscometer because of its paste-like, non-flowing consistency.

Using a viscosity reduction agent in this situation allows the reduction in viscosity of a gel cake without dilution with water. In this way a pumpable slurry is obtained which can be used as feed stock for a spray dryer or for supply to a mixer. Transport to another location by railroad tanker or by tank truck is also facilitated by making the slurry pumpable. Thereby, production costs are reduced since less water has to be evaporated or less manual handling is required.

EXAMPLE 2

Variations in Acacia Concentration

The following compositions contain about the same amount of added water and they show the effects of varying the concentration of the acacia in the mixture.

|  | A | B | C | D |
|---|---|---|---|---|
| Mg(OH)$_2$ wet gel (30%) | 266 g. | 266 g. | 266 g. | 266 g. |
| Acacia | — | 1 g. | 5 g. | 10 g. |
| Distilled water | 734 g. | 733 g. | 729 g. | 723 g. |
| Resultant viscosity | 2200 cps. | 1100 cps. | 1 cps. | 1 cps. |

EXAMPLE 3

Variations in Water and Acacia Concentrations

The following compositions show, compared to Example 2, the effects of adding more or less water and alternatively, no acacia:

|  | E | F | G |
|---|---|---|---|
| Mg(OH)$_2$ wet gel (30%) | 266 g. | 266 g. | 266 g. |
| Acacia | 6 g. | — | — |
| Distilled water | 61 g. | 200 g. | 67 g. |
| Resultant viscosity | 2000 cps. | 20000 cps. | too stiff to be measurable |

EXAMPLE 4

Effects of Other Viscosity Reducing Agents

The following compositions should be compared with the above compositions A F and G which have no fluidizing agents in them but do have some added water, mixed into the commercial gel.

| Mg(OH)$_2$ | + H$_2$O | + Fluidizing agent | = Resultant Viscosity |
|---|---|---|---|
| 266 g. | 724 g. | 10 g. citric acid | 220 cps. |
| 266 g. | 724 g. | 10 g. sodium citrate | 20 cps. |
| 266 g. | 724 g. | 10 g. sodium lauryl sulfate | 3.5 cps. |
| 266 g. | 170 g. | 30 g. sodium lauryl sulfate | 7.5 cps. |
| 266 g. | 728 g. | 6 g. dioctyl sodium succinate | 48 cps. |

EXAMPLE 5

Use of Different Commercial Gels

This shows that the addition of the same viscosity reducing agent in varying amounts, selected for different commercial gels, will produce products with consistent and substantially uniform viscosities.

|  | High Viscosity Gel | Med. Viscosity Gel |
|---|---|---|
| Mg(OH)$_2$ wet gel (30%) | 266.0 g. | 266.0 g. |
| Citric acid | 0.7 g. | 0.3 g. |
| Distilled water | 734.0 g. | 734.0 g. |
| Resultant viscosity | 1950 cps. | 1925 cps. |

EXAMPLE 6

Viscosity Lowering of Aluminum Hydroxide Gel

The following compositions illustrate the effectiveness of various fluidizing agents on aluminum hydroxide gels (30%):

| Al(OH)$_3$ | + H$_2$O | + Fluidizing Agent | = Resultant Viscosity |
|---|---|---|---|
| 550 g. | 440 g. | 10 g. acacia | 1600 cps. |
| 550 g. | 440 g. | 10 g. citric acid | 200 cps. |
| 550 g. | 440 g. | 10 g. sodium citrate | 1 cps. |
| 550 g. | 440 g. | 10 g. sodium lauryl sulfate | 3 cps. |
| 550 g. | 450 g. | (none) | 3800 cps. |

EXAMPLE 7

Concentrated Antacid Mixture Preparation

This shows that a mixture of commercial gels, of paste-like consistency, can be converted to a flowable viscosity.

| | |
|---|---|
| Magnesium hydroxide wet gel (30%) | 600 g. |
| Aluminum hydroxide wet gel (30%) | 190 g. |
| Acacia | 30 g. |
| Distilled water | 170 g. |
| Resultant viscosity (under stress) | 2000 cps. |

The above examples show that the putty-like consistency of commercial magnesium hydroxide and aluminum hydroxide wet gels is transformed to a flowable or fluidized consistency by the addition of relatively small amounts of either acacia, citric acid, sodium citrate, sodium lauryl sulfate or dioctyl sodium sulfosuccinate. This eliminates the need for adding water or heat or both to the wet gel in order to reduce its viscosity. The examples show that if water must be added to the wet gel to dilute it to a lower, desired viscosity this same viscosity can be obtained by the addition of much less water if one of the viscosity reducing agents of the invention is also added. This need for less water means that the fluidized suspension has a high concentration of the hydroxide but its lowered viscosity makes it possible to readily pour it or deliver it through pipes.

We claim:

1. The method of lowering the viscosity of a commercially available aqueous antacid gel cake which is supplied as a stiff, putty-like, non-flowing, bulk mass to physically transform it to a flowable consistency which can be pumped through a pipe, said gel cake being selected from the group consisting of:
   magnesium hydroxide,
   aluminum hydroxide and
   magnesium hydroxide and aluminum hydroxide mixtures, in which the antacid constitutes 25% to 35% w/w of the gel cake, which comprises mixing into said gel cake a fluidizing agent selected from the group consisting of:
   acacia,
   citric acid,
   sodium citrate,
   sodium lauryl sulfate and
   dioctyl sodium sulfosuccinate, in which said fluidizing agent is added so that it amounts to from 0.1% to 4% of the final total mixture.

2. The method of claim 1 in which the fluidizing agent which is used is acacia.

3. The method of claim 1 in which the fluidizing agent which is used is citric acid.

4. The method of claim 1 in which the fluidizing agent which is used is sodium citrate.

5. The method of claim 1 in which the fluidizing agent which is used is sodium lauryl sulfate.

6. The method of claim 1 in which the fluidizing agent which is used is dioctyl sodium sulfosuccinate.

* * * * *